| United States Patent [19] | | [11] | 4,187,245 |
|---|---|---|---|
| Redmore et al. | | [45] | Feb. 5, 1980 |

[54] HYDROXYPROPYLENE-AMINO-PHOSPHONIC-SULFONIC ACIDS

[75] Inventors: Derek Redmore, Ballwin; Frederick T. Welge, Affton, both of Mo.

[73] Assignee: Petrolite Corporation, St. Louis, Mo.

[21] Appl. No.: 966,249

[22] Filed: Dec. 4, 1978

Related U.S. Application Data

[63] Continuation of Ser. No. 582,862, Jun. 2, 1975, abandoned.

[51] Int. Cl.$^2$ .................... C07F 9/38; C07D 307/04; C07D 233/22; C07D 239/00
[52] U.S. Cl. .................................. 260/502.5; 210/58; 260/347.7; 260/501.12; 544/243; 548/352
[58] Field of Search ............. 260/502.5, 347.7, 501.12; 544/243; 548/352

[56] References Cited

U.S. PATENT DOCUMENTS

| 2,673,214 | 3/1954 | Bersworth et al. | 260/502.5 |
|---|---|---|---|
| 2,961,311 | 11/1960 | Bersworth et al. | 260/502.5 |
| 3,288,846 | 11/1966 | Irani et al. | 260/502.5 |
| 3,298,956 | 1/1967 | Irani et al. | 260/502.5 |
| 3,703,545 | 11/1972 | McCrary | 260/513 N |

FOREIGN PATENT DOCUMENTS

| 750481 | 6/1956 | United Kingdom | 260/502.5 |
|---|---|---|---|
| 1023785 | 3/1966 | United Kingdom | 260/502.5 |

*Primary Examiner*—Joseph E. Evans
*Attorney, Agent, or Firm*—Sidney B. Ring; Hyman F. Glass

[57] ABSTRACT

This invention relates to compounds characterized by the presence of N-methyl, or substituted methyl, phosphonic acid and N-hydroxy-propylenesulfonic acid groups. These compounds contain at least one or more of each group and are bonded to the same or different amino groups. They are derived by reacting an amine with both (1) an epihalohydrin-bisulfite addition product and (2) with a carbonyl compound, such as formaldehyde, and phosphorous acid or its equivalent.

They have a wide variety of uses, for example as scale and corrosion inhibitors, iron oxide removers, chelating agents, etc.

11 Claims, No Drawings

HYDROXYPROPYLENE-AMINO-PHOSPHONIC-SULFONIC ACIDS

This is a continuation, of application Ser. No. 582,862, filed June 2, 1975, now abandoned.

The compounds of this invention may be presented by the following idealized formula

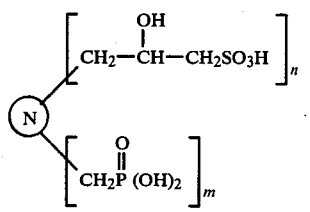

where Ⓝ is an amino moiety and n and m are at least 1, such as 1-5, for example from 1-3, but preferably 1.

In the case of a monoamine, n and m are 1. In the case of polyamine n and m can vary widely depending on the number of amino groups. Theoretically, the sum of n+m can be equal to the number of replaced amino hydrogens. In general, the sulfonic acid groups are 1-2 or more and the phosphonic acid groups are 1-5 or more.

Any amine capable of reacting with an epihalohydrin-bisulfate reaction product (HBS) can be employed, for example any amine having at least one primary amino group. Where the amine has more than one primary amino group, the number of sulfonic acid groups in the product will depend on the moles of HBS employed, for example $NH_2-Z-NH_2 \xrightarrow{1M}$

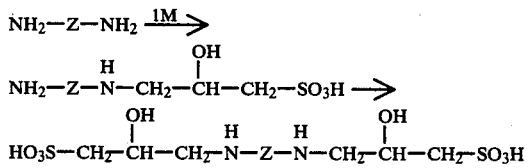

Theoretically, some or all of the remaining nitrogen-bonded hydrogens can be converted to the methyl phosphonic acid depending on the stoichiometry of the reactants.

Any amino group having a reactive N-hydrogen group which is capable of reacting with a carbonyl compound and phosphorous acid or equivalent can be reacted to yield the compounds of this invention.

The aminomethyl phosphonic acids of this invention and their salts may be prepared by various methods. One method comprises reacting (1) an amine having reactive hydrogens attached to a nitrogen atom, (2) a carbonyl compound such as an aldehyde or a ketone and (3) phosphorous acid, usually in the form of the dialkyl phosphite. The free N-aminomethyl phosphonic acids and their salts may be prepared by hydrolysis of the phosphonic ester under acid conditions such as with strong mineral acid such as HCl and the like.

These may be illustrated by the following reaction:

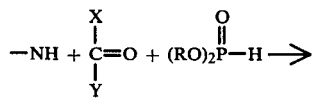

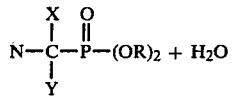

In the above equation X and Y are hydrogen or a substituted group such as an alkyl or aryl group, etc.

Phosphonic esters are converted to phosphonic acids or salts thereof according to the following reaction:

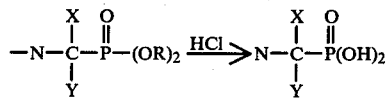

and other corresponding reactions.

Salts of these can also be prepared, for example salts containing metal, ammonium, amine, etc. groups such as sodium, potassium, triethanolamine, diethanolamine.

A second method comprises reacting (1) an amine, (2) a carbonyl compound such as aldehyde or a ketone and (3) phosphorous acid preferably in presence of a strong mineral acid such as hydrochloric acid. This method yields the aminomethyl phosphonic acids directly.

This may be illustrated by the following reaction:

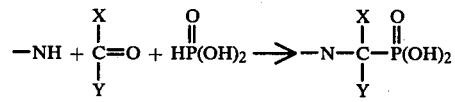

The general synthetic procedure involves three steps: (1) the reaction of an epihalohydrin with a bisulfite salt to form HBS, (2) reaction of a primary amine with HBS to form a γ-amino sulfonic acid and (3) reaction of this molecule with formaldehyde and phosphorous acid.

These products may be illustrated by the general formula

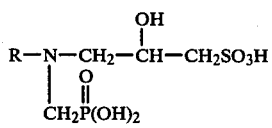

where R= alkyl, $-CH_2P(OH)_2$,
$\qquad$ aminoalkyl, etc.

The reaction sequence utilized is as follows:

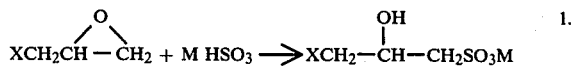

X = halogen, preferably Cl
M = metal salt, preferably sodium

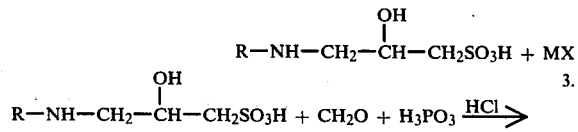

-continued

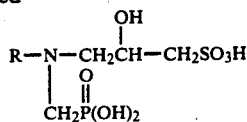

This reaction is applicable to a wide range of amines; thus R can be alkyl such as $CH_3$, $C_2H_5$, $C_3H_7$, $C_4H_9$, $C_6H_{13}$, $C_8H_{17}$, $C_{12}H_{25}$, $C_{18}H_{37}$, etc., straight chained or branched such as isopropyl, 2-ethyl hexyl, etc., cyclic aliphatic groups such as cyclopentyl, cyclohexyl.

Other amines which can be reacted include polyamines such as polyalkylene polyamines for example of the formula

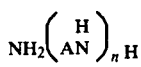

where A is alkylene for example having 2–10 carbons or more and n=1 to 10 or more, for example diamines such as ethylene diamine, propylene diamine, diethylene triamine, N-substituted 1,3-propylene diamines, etc.

Amines suitable for this process include the following:
n-Butylamine
2-ethyl hexyl amine
Monoisopropanolamine
Hexylamine
Heptylamine
Octylamine
Decylamine
Furfurylamine
Dodecylamine
Monoethanolamine
n-Amylamine
Sec-amylamine
2-amino-4-methylpentane
4-amino-2-butanol
5-isopropylamino-1-pentanol Also, high molecular weight aliphatic amines known as Armeen 10, Armeen 16D, Armeen HTD, Armeen 18D, and Armeen CD can be used ($RNH_2$).

Other amines include:
2-amino-2-methyl propanol
2-amino-2-methyl-1,3-propanediol
2-amino-2-ethyl-1,3-propanediol
3-amino-2-methyl-propanol
2-amino-1-butanol
3-amino-2,2-dimethyl-1-propanol
2-amino-2,3-dimethyl-1-propanol
2,2-diethyl-2-amino ethanol
2,2-dimethyl-2-amino ethanol
3-amino-1,2-butanediol
4-amino-1,2-butanediol
2-amino-1,3-butanediol
4-amino-1,3-butanediol
2-amino-1,4-butanediol
3-amino-1,4-butanediol
1-amino-2,3-butanediol Amines having ring structures include cyclohexylamine, and various comparable amines with alkyl substituents in the ring.

A wide variety of polyamines also can be employed. These include the polyalkylene polyamines such as of the formula:

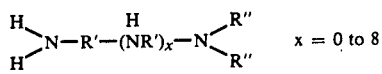

in which R" is hydrogen, alkyl, cycloalkyl, aryl, or aralkyl and R' is a divalent radical such as:

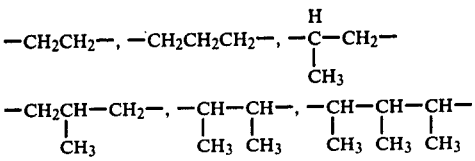

Examples of suitable polyamines include:
Ethylenediamine
Diethylenetriamine
Triethylenetetramine
Tetraethylenepentamine
Propylenediamine
Dipropylenetriamine
Tripropylenetetramine
Butylenediamine
Aminoethylpropylenediamine
Aminoethylbutylenediamine

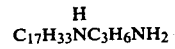

Other polyamines in which the nitrogen atoms are separated by a carbon atom chain having 4 or more carbon atoms include the following: Tetramethylenediamine, pentamethylenediamine, hexamethylenediamine, etc.

If desired, one can prepare a variety of reactants having two or more amino groups and at least one hydroxyl group. One may use modifications of procedures or the procedures themselves as described in U.S. Pat. Nos. 2,046,720, dated July 7, 1936, to Bottoms; 2,048,990 dated July 28, 1936, to Britton et al.; 2,447,821 dated Aug. 24, 1949, to Sankus; and 1,985,885 dated Jan. 1, 1935, to Bottoms. Examples include the following:

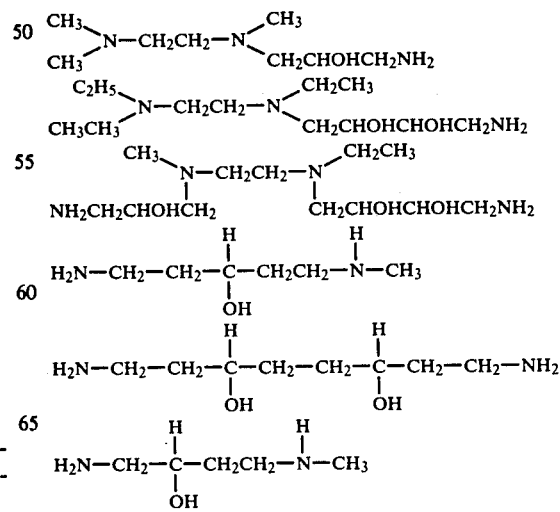

-continued

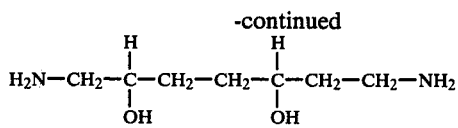

Other suitable amines are exemplified by ethylenebisoxypropylamine, $$\begin{array}{l}CH_2OCH_2CH_2CH_2NH_2\\|\\CH_2OCH_2CH_2CH_2NH_2\end{array}$$

Another example of polyamines which may be employed as a reactant is the kind described as "Duomeens."

Duomeen is a trademark designation for certain diamines. Duomeen has the following general formula:

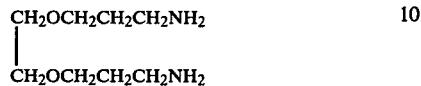

R is an alkyl group derived from a fatty acid or from the mixed fatty acids as obtained from certain oils. The specific Duomeen and the source of the radical R are as follows:

Duomeen 12, R=lauric
Duomeen C, R=Coconut oil fatty acid

Similarly, a commparable diamine, presumably obtained from Rosin Amine D and acrylonitrile, can be prepared. The structure of Rosin Amine D is as follows:

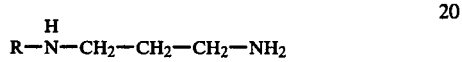

Polyamines from monoamines and cyclic imines, such as ethylene imine.

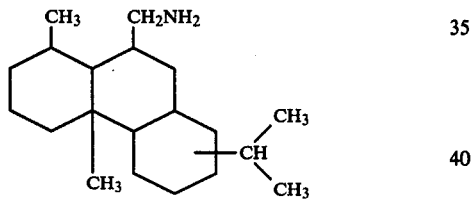
N-octyl ethylenediamine

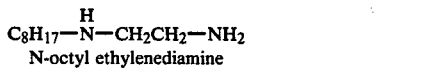
N-tetradecyl ethylenediamine

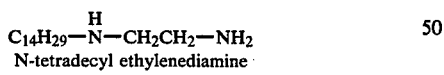
N-hexadecylethylenediamine

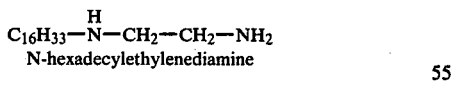
N-dodecyl triethylenetetramine

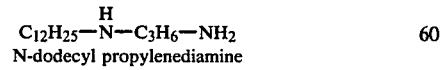
N-dodecyl propylenediamine

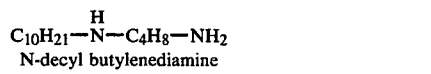
N-decyl butylenediamine

It is to be noted that all the above examples show high molal groups, i.e., 8 carbon atoms or more. The same derivatives in which methyl, ethyl, propyl, butyl, amyl, hexyl groups, or the like, appear instead of octyl, decyl, etc., are equally satisfactory.

Cyclic amidines, such as imidazolines and tetrahydropyrimidines, having an amino side chain can be reacted, for example:

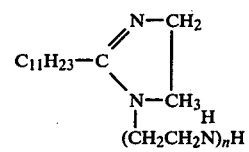
1-polyethyleneamine, 2-undecylimidazoline

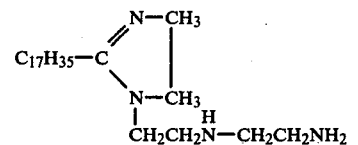
1-diethylene diamine, 2-heptadecylimidazoline

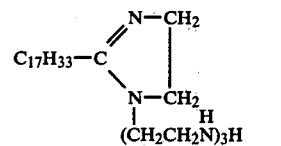
1-triethylenetriamine, 2-oleylimidazoline

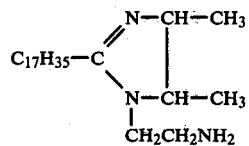
1-amino ethyl, 2-heptadecyl-4,5,dimethylimidazoline

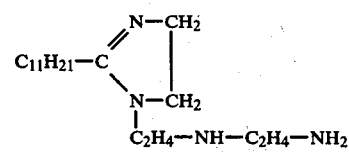
1-diethylenediamine, 2-undecylenecylimidazoline

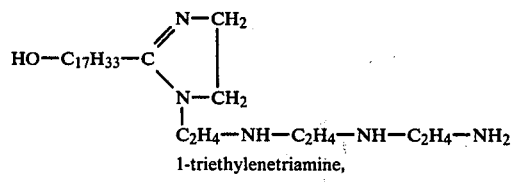
1-triethylenetriamine,
2-hydroxyheptadecylenecylimidazoline

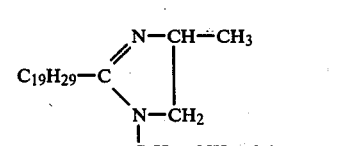
1-aminopropylaminopropyl,
2-abietyl, 4-methylimidazoline

Tetrahydropyrimidines from monocarboxylic acids and trimethylenepolyamines.

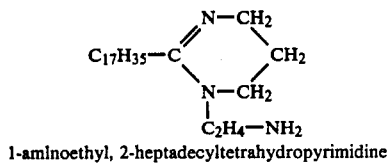

1-aminoethyl, 2-heptadecyltetrahydropyrimidine

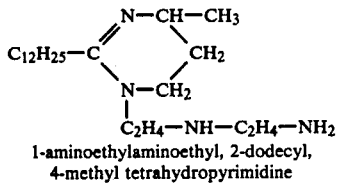

1-aminoethylaminoethyl, 2-dodecyl,
4-methyl tetrahydropyrimidine (1) The reaction between the epihalohydrin and the bisulfite salt is facile and takes place at 20° to 100° C. to form HBS. (2) The reaction between amines and HBS is very facile and occurs quite readily at temperatures from 30°–70° in a solvent such as methanol. Step (3) takes place at low pH and is most conveniently performed in aqueous HCl. Thus the amino sulfonate and phosphorous acid are heated in hydrochloric acid during the addition of formaldehyde usually at reflux.

The following examples illustrate the procedures. All temperatures are °C.

EXAMPLE 1

Preparation of 3-chloro-2-hydroxypropyl-sulfonic acid sodium salt

To a solution of sodium bisulfite (10 moles) in water (2500 ml) held at 80°–90° C. was added epichlorohydrin (10 moles) during 45 mins. Upon completion of the addition the mixture was heated at reflux for 1 hour. Upon cooling crystalline 3-chloro-2-hydroxypropyl-sulfonic acid sodium salt separated mp 253°–6° (decomp).

EXAMPLE 2

The chloropropylsulfonic acid of Example 1 (98 g; 0.5 mole) in water (130 g) was mixed with a 70% aqueous ethylamine solution (32 g; 0.5 mole) and heated at reflux for 1 hour. Evaporation of the water yield crude ethylaminosulfonic acid. Crystallization from methanol gave pure sulfonic acid of structure

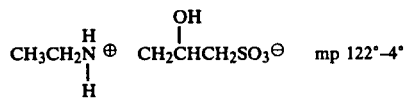

Anal. Found N, 6.95; S, 17.40; Calculated N, 7.65; S, 17.49.

EXAMPLE 3

The propylsulfonic acid of Example 1 (0.5 mole) in water (229 g) was heated with butylamine (36.5 g; 0.5 mole) for 1 hour at reflux. The crude aminosulfonic acid was obtained by evaporation of the water. Recrystallization from methanol yielded pure aminosulfonic acid mp 143°–5°

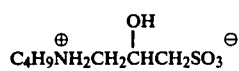

Anal. Found N, 6.08; S, 15.30; Calculated N, 6.63; S, 15.17.

EXAMPLE 4

In the manner of Example 2 n-hexylamine was reacted with 3-chloro-2-hydroxypropylsulfonic acid to yield

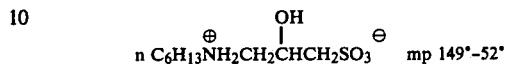

Anal. Found N, 5.58; S, 14.38; Calculated N, 5.85; S, 13.39.

EXAMPLE 5

In the manner of Example 2 cyclohexylamine was reacted with 3-chloro-2-hydroxypropylsulfonic acid to yield the N-cyclohexyl compound mp 166°–170°

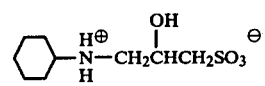

Anal. Found N, 5.85; S, 13.63; Calculated N, 5.90; S, 13.50.

EXAMPLE 6

In the manner of Example 2 t-octylamine was reacted with 3-chloro-2-hydroxypropylsulfonic acid to yield

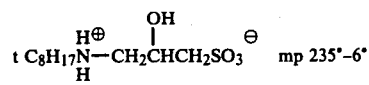

Anal. Found S, 11.73; Calculated S, 11.85.

EXAMPLE 7

To a solution of ethylene diamine (30 g; 0.5 mole) in water (100 ml) was added 3-chloro-2-hydroxypropyl-sulfonic acid (98 g; 10.5 mole) in water (200 ml) and the mixture heated under reflux for 1 hour. Evaporation of the solvent yielded the aminopropyl sulfonic acid of the formula

Analysis: Found N, 11.16; S, 14.81; Calculated N, 11.41; S, 16.2.

EXAMPLE 8

The procedure of Example 7 was repeated using a mole ratio of 1:2 to yield as the product

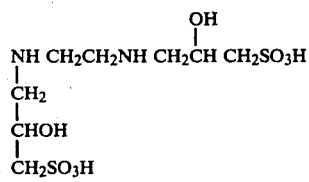

EXAMPLE 9

By the procedure of Example 7 diethylene triamine (0.5 mole) was reacted with the propylsulfonic acid (0.5 mole) of Example 1 to yield

EXAMPLE 10

By the procedure of Example 7 diethylene triamine (0.25 mole) was reacted with the propylsulfonic acid (0.5 mole) of Example 1 to yield

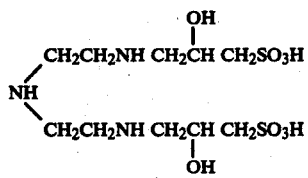

The following examples illustrate the preparation of amino-methylene phosphoric acids from the aminosulfonic acid derivatives of Examples 2–10.

EXAMPLE 11

The aminosulfonic acid of Example 2 (0.2 mole) was dissolved in 18% hydrochloric acid (60 ml) and phosphorus acid (16.4 g; 0.2 mole) added. After heating to gentle reflux (103°) 37% formaldehyde (25 g; 0.3 mole) was added during 1 hour. The reaction was complete after heating at reflux for 4 hours. Evaporation of the aqueous acid and crystallization yielded the aminosulfonic phosphonic acid of the formula:

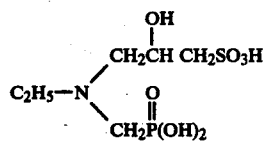

Anal. Found N, 5.10; P, 11.30; Calculated N, 5.05; P, 11.19.

EXAMPLE 12

The aminosulfonic acid of Example 3 (0.15 mole) and phosphorous acid (12.3 g; 0.15 mole) dissolved in 18% hydrochloric acid (50 ml) and heated to gentle reflux. To this solution was added 37% formaldehyde (19 g) during 45 mins. and the mixture heated at reflux for 3 hours to complete reaction. Evaporation of the aqueous acid and crystallization yielded the aminosulfonic phosphonic acid of the following formula:

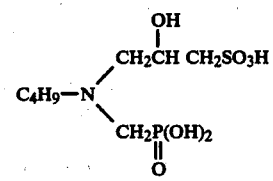

The product was characterized nmr and the following analysis:

Found N, 4.13; P, 10.07; Calculated N, 4.59; P, 10.16.

EXAMPLE 13

The aminosulfonic acid derived from n hexylamine (Example 4) (0.2 mole) was converted into the corresponding sulfonic-phosphonic acid by the procedure of Example 11.

The structure was shown by nmr to be:

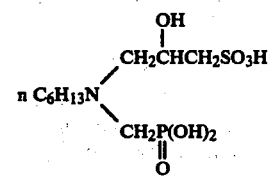

Analysis: Found N, 4.33; P, 9.07; Calculated N, 4.19; P, 9.28.

EXAMPLE 14

The aminosulfonic acid from cyclohexylamine (Example 5) was converted by the procedure of Example 11 to the corresponding phosphonic acid.

Analysis: Found N, 4.10; P, 9.33; Calcuated N, 4.22; P, 9.37.

EXAMPLE 15

The aminosulfonic acid of Example 6 derived from t octylamine was converted into the corresponding phosphonic acid by the method of Example 11. The structure of the product by nmr was shown to be

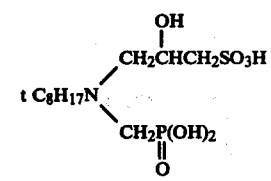

Analysis: Found N, 3.07; P, 8.27; Calculated: N, 3.88; P, 8.59.

EXAMPLE 16

The mono sulfonic acid derived from ethylene diamine (Example 7) was reacted with three equivalents of phosphorous acid and formaldehyde by the procedure of Example 11.

The product is represented by the formula

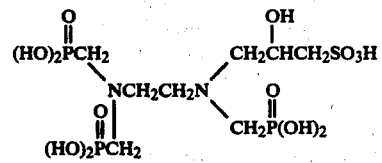

Analysis: Found P, 19.47; Calculated P, 19.40.

EXAMPLE 17

The disulfonic acid derived from ethylene diamine (Example 8) was reacted under the conditions of Example 11 with two equivalents of phosphorous acid and formaldehyde to yield the sulfonic/phosphonic acid below as the major product:

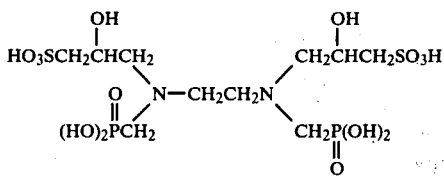

Analysis: Found N, 5.45; S, 11.43; P, 10.4; Calculated N, 5.34; S, 12.21; P, 11.8.

EXAMPLE 18

The monosulfonic acid of Example 9 was reacted with four equivalents of formaldehyde and phosphorous acid according to the procedure of Example 12 to yield the following product

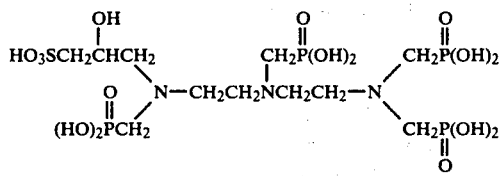

Analysis: Found P, 19.60; Calculated P, 20.10.

EXAMPLE 19

The disulfonic acid of Example 10 was reacted with three equivalents of phosphorous acid and formaldehyde by the procedure of Example 11. The product is a mixture, the major component of which is shown as follows:

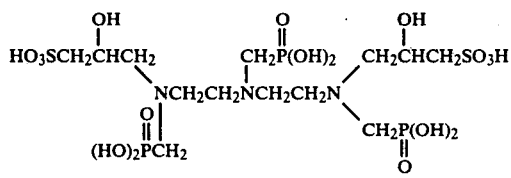

Analysis: Found P, 15.0; S, 10.09; Calculated: P, 14.1; S, 9.68.

USE AS SCALE INHIBITOR

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal. Scale-forming compounds can be prevented from precipitating by inactivating their cations with chelating of sequestering agents, so that the solubility of their reaction products is not exceeded. Generally, this approach requires many times of much chelating or sequestering agent as cation present, and the use of large amounts of treating agent is seldom desirable or economical.

More than twenty-five years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compound that has sequestering powers does not predictably have threshold inhibiting properties. For example, ethylenediamine tetracetic acid salts are powerful sequesterants but have no threshold activities.

We have now discovered a process for inhibiting scale such as calcium, barium and magnesium carbonate, sulfate, silicate, etc., scale which comprises employing threshold amounts of the compositions of this invention.

In general it is preferred that at least 50% but preferably at least 80% of the nitrogen-bonded hydrogens of the polyamine be replaced by sulfonate or phosphonate groups.

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 ppm and are preferably used in concentrations of less than 25 ppm.

The compounds of the present invention (e.g., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 ppm to about 50,000 ppm of scale-forming salts. The compounds of the present invention effectively inhibit scale formation when present in an amount of from 0.1 to about 100 ppm, and preferably 0.2 to 25 ppm wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 ppm. There is no reason to believe that this is the minimum effective concentration. The scale inhibitors of the present invention are effective in both brine, such as sea water, and acid solutions.

Calcium Scale Inhibition Test

The procedure utilized to determine the effectiveness of scale inhibitors in regard to calcium scale is as follows:

Several 50 ml. samples of a 0.04 sodium bicarbonate solution are placed in 100 ml. bottles. To these solutions is added the inhibitor in various known concentrations. 50 ml. samples of a 0.02 M $CaCl_2$ solution are then added.

A total hardness determination is then made on the 50—50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

| | Calcium Scale Inhibition | |
|---|---|---|
| Compound | Concentration | % Inhibition |
| Example 7 | 50 ppm | 50% |
| Example 8 | 50 ppm | 45% |
| Example 9 | 50 ppm | 45% |
| Example 10 | 25 ppm | 45% |
| Example 16 | 10 ppm | 91% |
| Example 16 | 25 ppm | 100% |
| Example 17 | 15 ppm | 72% |
| Example 17 | 25 ppm | 96% |
| Example 17 | 50 ppm | 100% |
| Example 19 | 25 ppm | 86% |
| Example 19 | 50 ppm | 100% |

Other uses include the following:
Use as corrosion inhibitors
Use as iron chelating agents, particularly to dissolve iron oxide deposits, in cooling water towers, etc.

We claim:

1. A compound containing one to five of each of the following amino nitrogen-bonded groups:

and

where R' and R" are hydrogen or alkyl and M is hydrogen or a salt ion selected from alkali metal, ammonium, alkaline earth metal and the ammonium form of triethanolamine and diethanolamine, the nitrogen to which said groups are bonded being at least one amino nitrogen of a moiety which, with hydrogen replacing said nitrogen bonded groups (I) and (II), is an amine which contains hydrogen attached to nitrogen and is selected from the group consisting of monoamines of the formula $RNH_2$, where R is alkyl or cycloalkyl, alkanolamines, polyamines selected from alkylene polyamines and polyalkylene polyamines and said polyamines substituted in a terminal nitrogen by alkyl, cycloalkyl, aryl or aralkyl, furfurylamine, ethylenebisoxypropylamine, and cyclic amidines having an amino side chain.

2. The compound of claim 1 where the

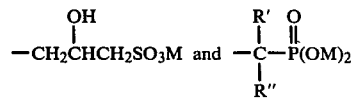

groups are bonded to the same nitrogen atom.

3. The compound of claim 2 of the formula

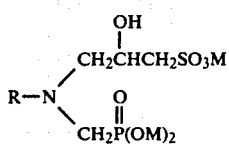

where R is defined in claim 1.

4. The compound of claim 1 where the compound has at least 2 nitrogen atoms.

5. The compound of claim 4 where the moiety with hydrogen replacing said groups (I) and (II) has the formula

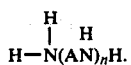

where A is alkylene and where n=1-4.

6. The compound of claim 5 where in at least one instance the

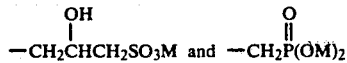

groups are bonded to the same nitrogen.

7. The compound of claim 5 where the compound contains no nitrogen-bonded hydrogens.

8. The compound of claim 6 which is derived from ethylene diamine or diethylene triamine.

9. The compound of claim 8 having the formula

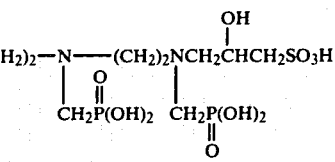

10. The compound of claim 8 having the formula

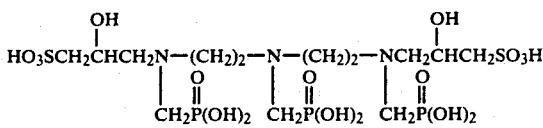

11. The compound of claim 1 having the formula

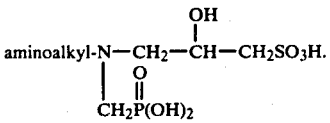

* * * * *